US012145980B2

(12) United States Patent
Kalergis Parra et al.

(10) Patent No.: US 12,145,980 B2
(45) Date of Patent: Nov. 19, 2024

(54) MONOCLONAL ANTIBODIES SPECIFIC FOR THE PB2 ANTIGEN OF THE HUMAN INFLUENZA A VIRUS (FLU), NUCLEOTIDE SEQUENCES, METHOD AND DIAGNOSTIC KIT FOR FLU INFECTION

(71) Applicant: PONTIFICIA UNIVERSIDAD CATOLICA DE CHILE, Santiago (CL)

(72) Inventors: Alexis Mikes Kalergis Parra, Santiago (CL); Susan Marcela Bueno Ramirez, Santiago (CL)

(73) Assignee: PONTIFICIA UNIVERSIDAD CATOLICA DE CHILE, Santiago (CL)

( * ) Notice: Subject to any disclaimer, the term of this patent is extended or adjusted under 35 U.S.C. 154(b) by 818 days.

(21) Appl. No.: 17/418,608

(22) PCT Filed: Dec. 27, 2019

(86) PCT No.: PCT/CL2019/050155
§ 371 (c)(1),
(2) Date: Jun. 25, 2021

(87) PCT Pub. No.: WO2020/132772
PCT Pub. Date: Jul. 2, 2020

(65) Prior Publication Data
US 2022/0119503 A1    Apr. 21, 2022

(30) Foreign Application Priority Data
Dec. 28, 2018  (CL) .................................. 3871-2018

(51) Int. Cl.
*C07K 16/10* (2006.01)
*A61K 39/00* (2006.01)
*A61P 31/16* (2006.01)
*G01N 33/533* (2006.01)
*G01N 33/543* (2006.01)
*G01N 33/569* (2006.01)

(52) U.S. Cl.
CPC .......... *C07K 16/1018* (2013.01); *A61P 31/16* (2018.01); *G01N 33/533* (2013.01); *G01N 33/543* (2013.01); *G01N 33/56983* (2013.01); *A61K 2039/505* (2013.01); *C07K 2317/51* (2013.01); *C07K 2317/515* (2013.01); *C07K 2317/92* (2013.01); *G01N 2333/11* (2013.01); *G01N 2469/10* (2013.01)

(58) Field of Classification Search
CPC ............ C07K 16/1018; C07K 2317/51; C07K 2317/515; C07K 2317/92; C07K 2317/54; C07K 2317/55; A61P 31/16; G01N 33/533; G01N 33/543; G01N 33/56983; G01N 2333/11; G01N 2469/10; A61K 2039/505
See application file for complete search history.

(56) References Cited

U.S. PATENT DOCUMENTS 9,650,434 B2    5/2017   Chen et al.

FOREIGN PATENT DOCUMENTS

| AU | 2008309939 B2 | 11/2013 |
| JP | 2013540701 A | 11/2013 |
| JP | 2015189715 A * | 11/2015 |
| WO | 2006051069 A2 | 5/2006 |
| WO | 2009046983 A1 | 4/2009 |
| WO | 2012045001 A2 | 4/2012 |

OTHER PUBLICATIONS

Ochoa M, Bárcena J, de la Luna S, Melero JA, Douglas AR, Nieto A, Ortín J, Skehel JJ, Portela A. Epitope mapping of cross-reactive monoclonal antibodies specific for the influenza A virus PA and PB2 polypeptides. Virus Res. Aug. 1995;37(3):305-15. (Year: 1995).*
Cosmo Bio Co., Ltd., Catalog No. KAST-MA001, KAST-MA003, 34 pages, Jul. 2018.
Ural Chaisri, et al., "Evolution of Therapeutic Antibodies, Influenza Virus Biology, Influenza, and Influenze Immunotherapy", BioMed Research International, vol. 2018, Article ID 9747549, 24 pages, 2018.
M. Hatta, et al., "Mapping of Functional Domains on the Influenza a Virus RNA Polymerase PB2 Molecule Using Monoclonal Antibodies", Arch Virol, vol. 145, No. 9, pp. 1947-1961, 2000.
International Search Report and Written Opinion for Corresponding International Application No. PCT/CL2019/050155 dated Apr. 3, 2020 and English translation.

* cited by examiner

*Primary Examiner* — Nicole Kinsey White
*Assistant Examiner* — Samadhan Jaising Jadhao
(74) *Attorney, Agent, or Firm* — LUCAS & MERCANTI, LLP

(57) ABSTRACT

Generation of monoclonal antibodies, or fragments thereof, that recognize the PB2 protein of the human influenza A virus (Flu), where the monoclonal antibodies or fragments thereof, has a heavy chain variable region and light chain variable region. Furthermore, a diagnostic method is provided to detect Flu infections in biological samples of nasopharyngeal secretions, using monoclonal antibodies in diagnostic kit format.

9 Claims, 5 Drawing Sheets
Specification includes a Sequence Listing.

Figure 2
A
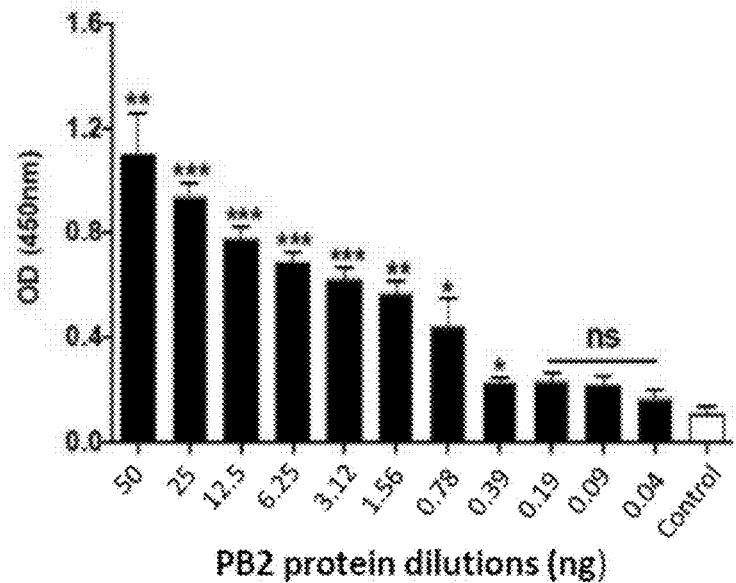
B
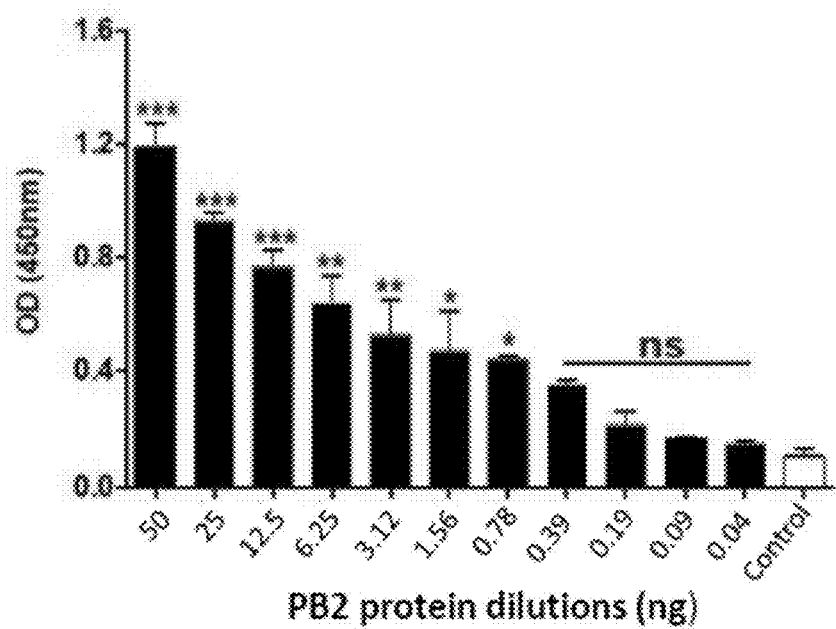

Figure 3
A
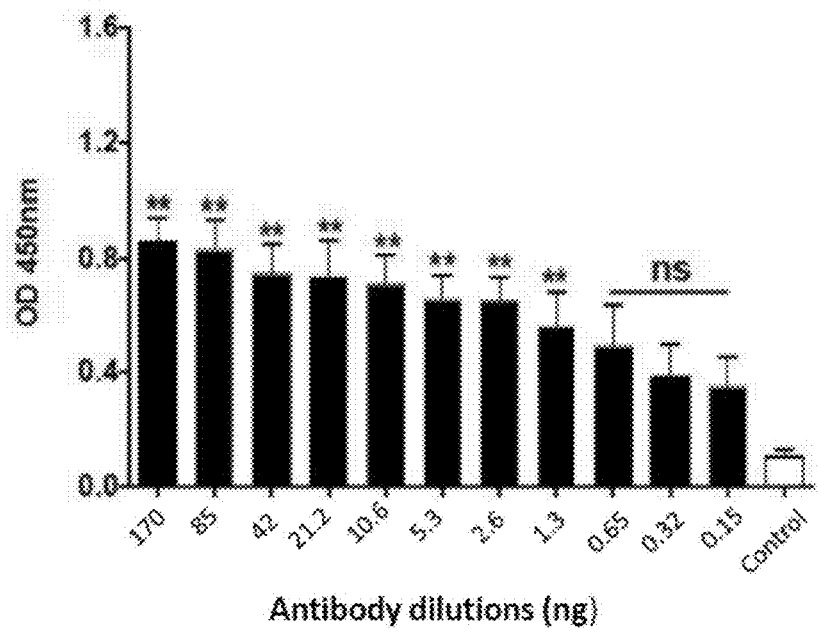
B
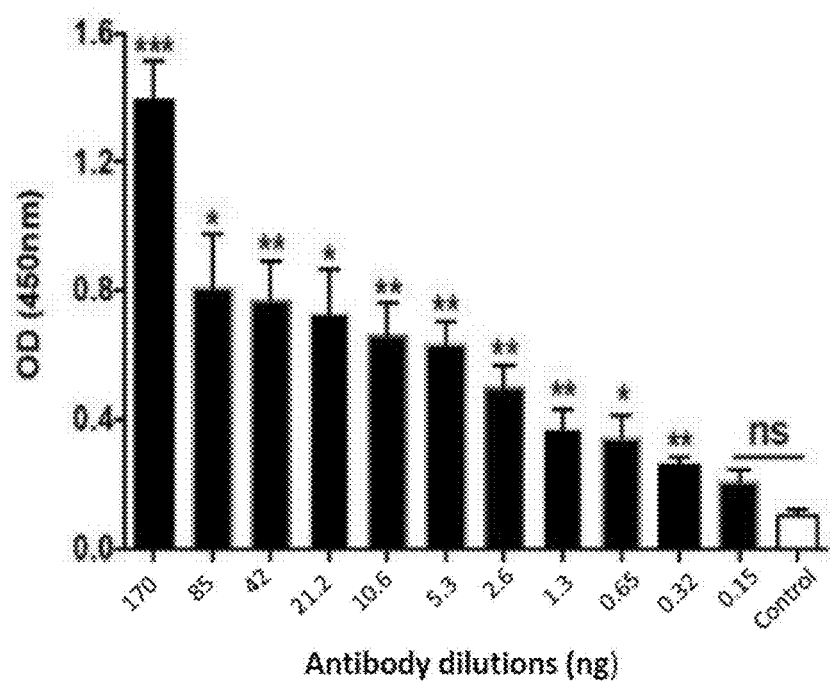

SEQUENCE LISTING

```
<160> NUMBER OF SEQ ID NOS: 12

<210> SEQ ID NO 1
<211> LENGTH: 16
<212> TYPE: PRT
<213> ORGANISM: Artificial Sequence
<220> FEATURE:
<223> OTHER INFORMATION: Synthetic - Hybridoma 1A3E2 - Anti PB2 Flu
      CDRLC 1

<400> SEQUENCE: 1

Arg Ser Ser Gln Ser Leu Leu Asp Ser Asp Gly Lys Thr Tyr Leu Asn
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Synthetic - Hybridoma 1A3E2 - Anti PB2 Flu
      CDRLC 2
```

```
<400> SEQUENCE: 2

Leu Val Ser Lys Leu Asp Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic - Hybridoma 1A3E2 - Anti PB2 Flu
      CDRLC 3

<400> SEQUENCE: 3

Trp Gln Gly Thr His Phe Pro Phe Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic - Hybridoma 1A3E2 - Anti PB2 Flu
      CDRHC 1

<400> SEQUENCE: 4

Asp Tyr Tyr Met Tyr
1               5

<210> SEQ ID NO 5
<211> LENGTH: 17
<212> TYPE: PRT
<213> ORGANISM: Artificial Sequence
<220> FEATURE:
<223> OTHER INFORMATION: Synthetic - Hybridoma 1A3E2 - Anti PB2 Flu
      CDRHC 2

<400> SEQUENCE: 5

Tyr Ile Ser Asp Gly Gly Ser Tyr Thr Tyr Tyr Gln Asp Asn Val Lys
1               5                   10                  15

Gly

<210> SEQ ID NO 6
<211> LENGTH: 13
<212> TYPE: PRT
<213> ORGANISM: Artificial Sequence
<220> FEATURE:
<223> OTHER INFORMATION: Synthetic - Hybridoma 1A3E2 - Anti PB2 Flu
      CDRHC 3

<400> SEQUENCE: 6

Asp Arg Asp Asp Tyr Asp Gly Tyr Tyr Val Met Asp Tyr
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Synthetic - Hybridoma 1A3E2 - Anti PB2 Flu
      CDRHC 1

<400> SEQUENCE: 7

Lys Ser Ser Gln Ser Leu Leu Asp Ser Asp Gly Lys Thr Tyr Leu Asn
1               5                   10                  15
```

```
<210> SEQ ID NO 8
<211> LENGTH: 7
<212> TYPE: PRT
<213> ORGANISM: Artificial Sequence
<220> FEATURE:
<223> OTHER INFORMATION: Synthetic - Hybridoma 2F11B1 - Anti PB2 Flu
      CDRLC 2

<400> SEQUENCE: 8

Leu Val Ser Lys Leu Asp Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic - Hybridoma 2F11B1 - Anti PB2 Flu
      CDRLC 3

<400> SEQUENCE: 9

Trp Gln Gly Thr His Phe Pro Tyr Thr
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic - Hybridoma 2F11B1 - Anti PB2 Flu
      CDRLC 1

<400> SEQUENCE: 10

Asp Tyr Tyr Met Tyr
1               5

<210> SEQ ID NO 11
<211> LENGTH: 17
<212> TYPE: PRT
<213> ORGANISM: Artificial Sequence
<220> FEATURE:
<223> OTHER INFORMATION: Synthetic - Hybridoma 2F11B1 - Anti PB2 Flu
      CDRHC 2

<400> SEQUENCE: 11

Tyr Ile Ser Asp Gly Gly Ser Tyr Thr Tyr Tyr Pro Asp Ser Val Lys
1               5                   10                  15

Gly

<210> SEQ ID NO 12
<211> LENGTH: 14
<212> TYPE: PRT
<213> ORGANISM: Artificial Sequence
<220> FEATURE:
<223> OTHER INFORMATION: Synthetic - Hybridoma 2F11B1 - Anti PB2 Flu
      CDRHC 3

<400> SEQUENCE: 12

Asp Gly Asp Tyr Asp Tyr Ser Tyr Tyr Tyr Ala Met Asp Tyr
1               5                   10
```

MONOCLONAL ANTIBODIES SPECIFIC FOR THE PB2 ANTIGEN OF THE HUMAN INFLUENZA A VIRUS (FLU), NUCLEOTIDE SEQUENCES, METHOD AND DIAGNOSTIC KIT FOR FLU INFECTION

CROSS REFERENCE TO RELATED APPLICATION

This Application is a 371 of PCT/CL2019/050155 filed on Dec. 27, 2019, which, in turn, claimed the priority of Chilean Patent Application No. 3871-2018 filed on Dec. 28, 2018, both applications are incorporated herein by reference.

DESCRIPTION OF THE INVENTION

Monoclonal antibodies, or fragments thereof are disclosed, that recognize the PB2 protein of the human influenza virus (Flu), where said monoclonal antibodies or fragments thereof comprise an antibody that comprises a light chain variable region where its CDR1 ($CDR_{LC1}$) is defined according to SEQ ID NO: 1, its CDR2 ($CDR_{LC2}$) is defined by SEQ ID NO: 2 and its CDR3 ($CDR_{LC3}$) corresponds to SEQ ID NO: 3, and a heavy chain variable region where its CDR1 ($CDR_{HC1}$) is defined according to SEQ ID NO: 4, its CDR2 ($CDR_{HC2}$) is defined by SEQ ID NO: 5 and its CDR3 ($CDR_{HC3}$) corresponds to SEQ ID NO: 6, or an antibody comprising a light chain variable region where its CDR1 ($CDR_{LC1}$) is defined according to SEQ ID NO: 7, its CDR2 ($CDR_{LC2}$) is defined by SEQ ID NO: 8 and its CDR3 ($CDR_{LC3}$) corresponds to SEQ ID NO: 9, and a heavy chain variable region where its CDR1 ($CDR_{HC1}$) is defined according to SEQ ID NO: 10, its CDR2 ($CDR_{HC2}$) corresponds to SEQ ID NO: 11 and its CDR3 ($CDR_{HC3}$) corresponds to SEQ ID NO: 12, where said antibody can be used as detection or capture antibody. Additionally, a method for diagnosing Flu infection in a biological sample is provided that uses monoclonal antibodies in diagnostic kit format to detect Flu, where said kit comprises at least one monoclonal antibody against Flu as previously described.

FIELD OF THE INVENTION

The present invention relates to monoclonal antibodies, or fragments thereof, that recognize the PB2 protein of the human influenza virus, useful for the development of diagnostic methods of influenza infection in humans.

BACKGROUND OF THE INVENTION

Influenza is an infectious disease of the respiratory tract caused by the human influenza virus. This virus is responsible for producing severe or mild respiratory symptoms, mainly affecting the areas of the nose, throat, bronchial tubes and occasionally the lungs. In general, clinical symptoms of influenza are similar to those of seasonal flu, however, symptoms can be variable and range from an asymptomatic infection to severe pneumonia that can lead to death.[1]. The virus is easily transmitted from person to person or through drops or small particles that have been expelled through the cough or sneeze of a sick person, which makes it spread quickly and be part of seasonal epidemics.

[1]1. www.who.int/csr/disease/swineflu/faq/es/#doesit

Influenza virus can be detected throughout the year, but its detection increases in the autumn-winter season, although time and duration can be variable.[2]. According to epidemiological statistics, in the United States in 2016, 310,000 people were hospitalized for complications related to influenza. In the same country, statistics indicate that this infection causes around 89,000 deaths annually. From the point of view of economic cost, losses due to human influenza viruses in the United States are estimated to reach an annual cost that ranges from 71 to 150 billion dollars[3].

[2] espanol.cdc.gov/enes/flu/about/season/flu-season.htm

[3] espanol.cdc.gov/enes/flu/about/disease/us_flu-related_deaths.htm

The most common diagnostic methods for the detection of Flu are called "Rapid Influenza Diagnostic Tests" (RIDT), these tests are based on the detection of Flu antigens (immunoassay) in swab or nasopharyngeal aspirate samples. These tests can give a result in a period of 15 to 20 minutes, however, they lack sensitivity and only confer a qualitative result (positive or negative), which can potentially be a false negative due to its low specificity[4].

[4] espanol.cdc.gov/enes/flu/professionals/diagnosis/rapidlab.htm

Until now, the standard technique for confirming an influenza virus infection corresponds to molecular analysis of reverse transcriptase polymerase chain reaction (RT-PCR). For example, Human Influenza Virus Real-Time RT-PCR Diagnostic Panel developed by the Center for Disease Control and Prevention (CDC) enables in vitro detection of influenza virus in respiratory tract samples from human patients exhibiting signs and symptoms of respiratory infection. This method detects influenza A and B viruses through the reaction of primers against genes encoding highly conserved proteins, such as matrix protein (M protein), nucleoprotein (NP protein) and non-structural protein (NS protein). This type of technique has disadvantages in terms of cost and optimization, since its implementation and start-up requires the acquisition of high-cost specialized equipment and reagents, as well as highly trained personnel.

Another common method for diagnosis is viral isolation in cell cultures. The problem with this type of technique is that it requires highly specialized equipment and personnel. On the other hand, it is a slow method that can deliver diagnostic results within 5 to 14 days after its initiation.

In the practice of clinical diagnosis, one of the main difficulties or problems is the sample itself, since a limited amount of it can be accessed, which also has a low antigen concentration and includes the presence of other proteins and cellular components that can interfere with the detection reaction.

Monoclonal antibodies have been previously described for the detection of human influenza virus antigens. In WO2012045001 (A2), for example, a human monoclonal antibody is disclosed that binds to the surface protein hemagglutinin. In U.S. Pat. No. 9,650,434B2a monoclonal antibody or antigen-binding fragment thereof is provided, which can specifically bind to HA1 domain of the hemagglutinin protein of influenza viruses H1 subtype and H5 subtype. In both documents, the proposed solution aims at a different antigen from the PB2 protein detection, and the efficiency, specificity and sensitivity of the antigen-antibody binding in clinical samples is not demonstrated.

Regarding detection of the Flu PB2 protein, JP2015189715 (A) provides a monoclonal antibody or an antigen-binding fragment thereof that binds to the PB2 subunit of RNA-dependent RNA polymerase. Sequences of the heavy chain variable regions and light chain variable regions of the antibody described therein differ substantially from the monoclonal antibodies' sequences part of the invention. On the other hand, JP2015189715 (A) does not perform antigen detection assays in human clinical samples, nor the specificity and sensitivity features of the antibodies is determined, in the context of clinical diagnosis. Let us remember that in clinical diagnostic conditions, biological samples that include very low concentrations of antigen are used, which hinders the specificity and sensitivity of the antigen-antibody reaction.

Therefore, a new alternative for the diagnosis of the human influenza virus is required that, unlike molecular diagnostic tests and cell culture tests that entail longer response times and a high cost for their implementation and maintenance, allows the detection of a wide variety of influenza types and subtypes quickly, sensitively, specifically and at a lower cost. Furthermore, even though until now monoclonal antibodies have been proposed for detection of other Flu proteins and even against PB2, these antibodies have only been evaluated in murine models and do not correspond in any case to a solution to the posed technical problem.

According to information provided, monoclonal antibodies that detect PB2 protein are proposed to be used in detection and rapid, efficient and accurate diagnosis in patients infected with Flu, where said antibodies specifically detect the protein in clinical samples at very low concentrations of the specific antigen (high sensitivity), even distinguishing the specific viral antigen in clinical samples that even include antigens from other respiratory viruses. Additionally, provided antibodies can form part of a diagnostic method and kit for the Flu diagnosis, where each antibody can be used in a versatile way as a detection antibody as well as a capture antibody.

DESCRIPTION OF THE INVENTION

The present invention relates to specific monoclonal antibodies against PB2 protein fragments thereof, of the human influenza virus. In particular, the invention corresponds to monoclonal antibodies or fragments thereof secreted by hybridoma cell lines called 1A3E2 and 2F11B1, that recognize the PB2 protein of the human influenza virus (Flu), where said monoclonal antibodies or fragments thereof comprise an antibody that comprises a light chain variable region where its CDR1 ($CDR_{LC1}$) is defined according to SEQ ID NO: 1, its CDR2 ($CDR_{LC2}$) is defined by SEQ ID NO: 2 and its CDR3 ($CDR_{LC3}$) corresponds to SEQ ID NO: 3, and a heavy chain variable region where its CDR1 ($CDR_{HC1}$) is defined according to SEQ ID NO: 4, its CDR2 ($CDR_{HC2}$) is defined by SEQ ID NO: 5 and its CDR3 ($CDR_{HC3}$) corresponds to SEQ ID NO: 6, or an antibody comprising a light chain variable region where its CDR1 ($CDR_{LC1}$) is defined according to SEQ ID NO: 7, its CDR2 ($CDR_{LC2}$) is defined by SEQ ID NO: 8 and its CDR3 ($CDR_{LC3}$) corresponds to SEQ ID NO: 9, and a heavy chain variable region where its CDR1 ($CDR_{HC1}$) is defined according to SEQ ID NO: 10, its CDR2 ($CDR_{HC2}$) corresponds to SEQ ID NO: 11 and its CDR3 ($CDR_{HC3}$) corresponds to SEQ ID NO: 12, where said antibody can be used as detection or capture antibody. Additionally, a method for diagnosing Flu infection in a biological sample is provided that uses monoclonal antibodies in diagnostic kit format to detect Flu, where said kit comprises at least one monoclonal antibody against Flu as previously described.

Antibodies described in the invention have important advantageous and remarkable technical features with respect to other antibodies and methods for detecting viral antigens already existing.

First, each virus has specific surface proteins, therefore, other diagnostic techniques based on monoclonal antibodies for other types of respiratory viruses are not comparable to the proposed invention. Detection specificity of antibodies against Flu PB2 protein respect to other viral antigens, for example against adenovirus pill protein, is demonstrated in the results provided in FIGS. 1A, 1B and 1C of the present application. From these results it is possible to conclude that the provided antibodies in the scope of the present application only recognize the Flu PB2 protein, and that in ELISA assays with ADV virus antigens no detection signal was observed.

Second, antibodies that are part of the scope of the invention allow specific detection of PB2 protein fragments thereof, in such a way that they do not compete with each other for the antigen-binding site, nor do they exert an impediment to simultaneously bind to it.

Third, they allow the detection of PB2 protein or fragments thereof with high sensitivity in samples containing a small antigen amount, such as nasopharyngeal swab samples, for example.

The proposed monoclonal antibodies are capable of detecting PB2 protein, a highly conserved protein. Strategy for detecting a conserved viral protein allows antibodies that are part of the scope of the invention to detect different types of human influenza, including influenza A, B and C.

When reference is made to CDR sequences in the present invention, these correspond to short sequences found in the variable domains of proteins that have antigen detection function. CDR sequences for the heavy chain ($CDR_{HC}$) and light chain ($CDR_{LC}$) of the antibodies secreted by hybridomas 1A3E2 and 2F11B1.

Monoclonal antibodies described can be used for Flu infection determination, diagnosis and/or detection assays. These antibodies can be used simultaneously to increase detection sensitivity of clinical samples where there is little quantity and availability of antigen. In this regard, it is also provided a Flu infection diagnosis method in a biological sample, which comprises contacting the biological sample with the monoclonal antibody against Flu PB2 protein or a fragment thereof according to the claim, and detecting the binding of the antibody with the antigen. Biological sample can be, but is not limited to, infected in vitro cells with Flu, nasal secretions, nasal washes, cerebrospinal fluid, pharyngeal secretions and/or bronchial washes or secretions. As part of the method, the assay used for the detection of antigen-antibody binding is selected from ELISA, luminex, immunofluorescence, immunohistochemistry, immunochromatography, flow cytometry, cell sorter, immunoprecipitation and/or Western blot.

Present invention also includes a diagnostic kit to detect the human influenza virus, which comprises: a monoclonal antibody against Flu PB2 protein or a fragment thereof, where said antibody can act as a capture or detection antibody, where particularly, the detection antibody is conjugated to a marker for its detection; a solid support to which the antibody is attached; and reagents for detecting the marker included in the detection antibody, such as fluorophores, biotin, radioisotopes, metals, and enzymes.

In the present invention when it refers to capture antibody, this corresponds to the antibody that specifically binds to the antigen. In the case of the detection antibody, this corresponds to the antibody to which a marker is conjugated to be detected by different tests such as immunochromatographic test, luminex, flow cytometry, immunofluorescence, radioimmunoassay, Western blot, Dot plot, ELISA, luminex, immunodiffusion. or immunoprecipitation.

Antibodies that are part of the present invention can act dually as a capture antibody or as a detection antibody when coupled to a detection marker. Detection marker will be conjugated to the detection antibody, and this can correspond, without limitation, to fluorophores, biotin, radioisotopes, metals and enzymes. Preferably, the detection antibody is conjugated to reporter system based on the detection of horseradish peroxidase (HRP) enzyme activity.

BRIEF DESCRIPTION OF THE DRAWINGS

FIG. 2: Sensitivity determination of monoclonal antibodies produced by 1A3E2 and 2F11B1 hybridomas in the detection of Flu PB2. ELISA plates were activated with 1:2 serial dilutions, starting with 50 ng of PB2 protein ending with 0.04 ng. Subsequently, the wells were incubated with the anti-PB2 antibodies from the 1A3E2 hybridoma, in an amount of 170 ng (A) and the 2F11B1 hybridoma in an amount of 170 ng (B). Non-activated wells were included as a negative control. Data shown in the graph express absorbance at 450 nm, emitted by the conversion of Tetramethylbenzidine substrate to a colored compound, catalyzed by Horseradish peroxidase (HRP) enzyme conjugated to anti-PB2 antibodies from 1A3E2 and 2F11B1 hybridomas in an amount of 170 ng (A and B). Values correspond to the standard deviation in absorbance average+/−emitted by each sample in at least two independent experiments. *P<0.05; P<0.01 and *P<0.001 by parametric student test comparing the results of well called control versus each of the dilutions of PB2 protein.

FIG. 3: Assay of serial dilutions of Flu anti-PB2 monoclonal antibodies produced by 1A3E2 and 2F11B1 hybridomas, for the detection of purified Flu antigens. ELISA plates were activated with 50 ng of Flu recombinant PB2 protein and antigen was detected with 11 serial dilutions of anti-1A3E2 PB2 antibodies (A) or 2F11B1 (B) 1:2, starting from a concentration of 3.4 µg/mL (170 ng per well). Values are expressed as standard deviation average+/−of the value of absorbance emitted at 450 nm of each duplicate sample, in at least two independent experiments. *P<0.05; P<0.01 and *P<0.001 by parametric student test comparing the results of well called control versus each dilution of PB2 protein.

Figure 1:
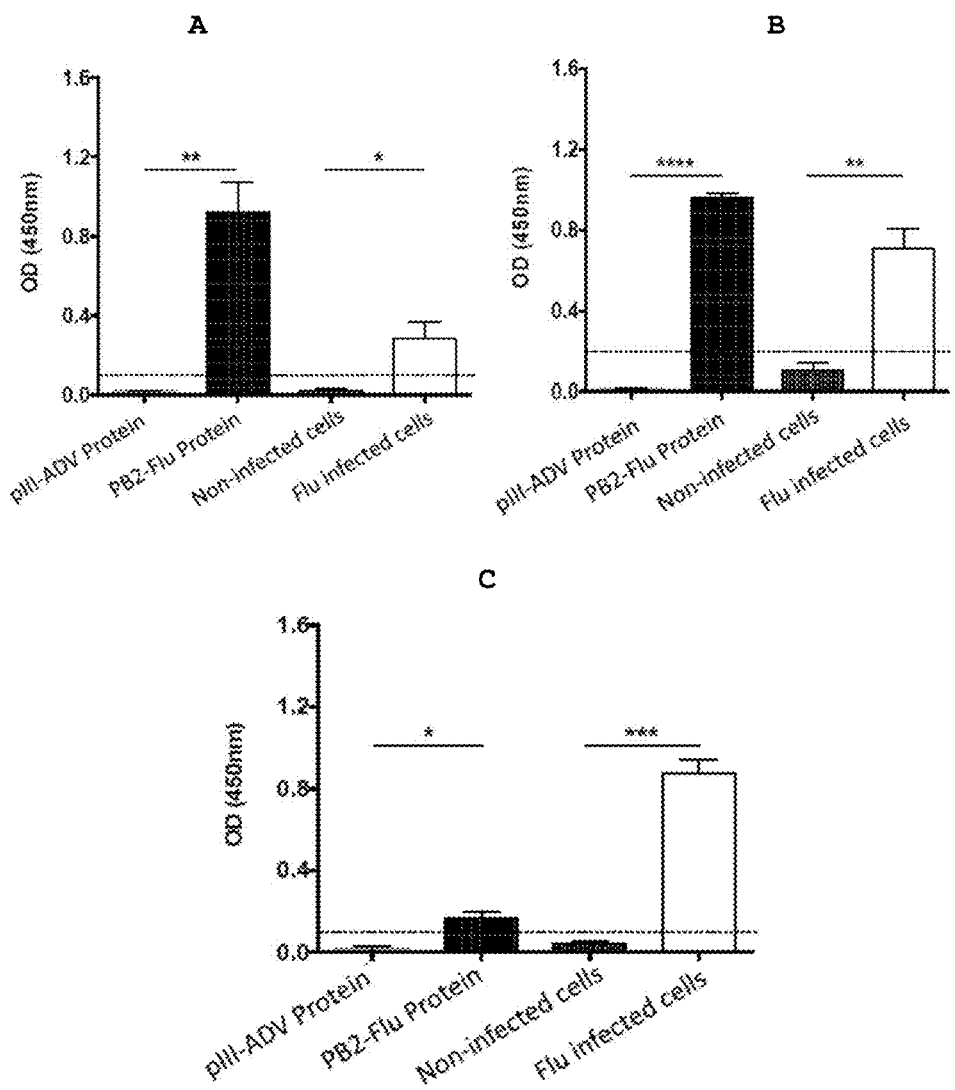
FIG. 1: Flu PB2 protein detection by monoclonal antibodies produced by 1A3E2 and 2F11B1 hybridomas, using an indirect ELISA assay. The plate was activated with 50 ng of purified Flu recombinant PB2 protein, 50 ng of ADV pIII protein (as a specificity control) and 20 µg of uninfected (used as a specificity control) and Flu-infected MDCK cells. Control wells with no antigen, with primary antibody, with HRP-conjugated anti-mouse IgG (not activated) and wells with no antigen or primary antibody, only with anti-mouse IgG (HRP), data not shown in the graph. Subsequently, wells were incubated with the anti-PB2 antibodies from the 1A3E2 hybridoma, in an amount of 170 ng (A), 2F11B1 hybridoma in an amount of 170 ng (B) and the commercial polyclonal antibody Anti-Influenza A virus PB2 protein antibody, catalog number GTX125926 (GeneTex) used in an amount of 170 ng (C). Data shown in the graph express detected absorbance (in OD, optical density) at 450 nm, emitted by the conversion of Tetramethylbenzidine substrate to a colored compound, catalyzed by Horseradish peroxidase (HRP)enzyme conjugated in a secondary anti-mouse IgG antibody that specifically bound antibodies secreted by GeneTex hybridomas 1A3E2, 4D8C6 and GTX125926 hybridomas. Values correspond to the standard deviation in absorbance average+/−emitted by each sample in at least two independent experiments. Where, *P<0.05; P<0.01; *P<0.001 and ****P<0.0001 by parametric student test comparing the results of the pIII-ADV protein versus those of PB2-Flu, and on the other hand comparing the uninfected versus infected cells.

EXAMPLES THAT MAKE IT POSSIBLE TO DEMONSTRATE THE DIFFERENT APPLICATIONS OF THE MONOCLONAL ANTIBODIES OF THE INVENTION

Example 1: Determination of the Nucleotide Sequence Encoding the Light (VL) and Heavy (VH) Chains of the Variable Region of Flu Anti-PB2 Antibody Secreted by 1A3E2 Hybridoma 1A3E2 hybridoma was grown in DMEM-high glucose culture medium supplemented with 3.7 g/L of Sodium Bicarbonate and 10% fetal bovine serum, at 37° C. (98.6° F.) with 10% $CO_2$, up to a cell density of 700,000 cells/mL. Total RNA of $3.5 \times 10^6$ cells was obtained, performing a treatment with Trizol compound (Invitrogen). 0.5 µg of RNA was used to generate the cDNA by reverse transcription reaction with the PrimeScript™ 1st Strand cDNA Synthesis kit, which uses isotype-specific universal primers. The antibody heavy and light chain were amplified according to the GenScript rapid amplification of cDNA ends (RACE) standard operating procedure (SOP). Amplified antibody fragments were separately cloned into a standard cloning vector. PCR colony was performed to identify clones which have the correct size inserts. At least five colonies with inserts of the correct size were sequenced for each fragment. Sequences of different clones were aligned and the consensus sequence of these clones was provided. Nucleotide sequences of heavy and light chains of antibodies secreted by 1A3E2 hybridoma were identified, being identified as SEQ ID NO. 1 and SEQ ID NO.3 for the case of heavy chains and SEQ ID NO. 2 and SEQ ID NO.4 for the case of light chains.

Example 2: Determination of the Nucleotide Sequence Encoding the Light (VL) and Heavy (VH) Chains of the Variable Region of Flu Anti-PB2 Antibody Secreted by 2F11B1 Hybridoma 2F11B1 hybridoma was grown in DMEM-high glucose culture medium supplemented with 3.7 g/L of Sodium Bicarbonate and 10% fetal bovine serum, at 37° C. (98.6° F.) with 10% $CO_2$, up to a cell density of 700,000 cells/mL. Total RNA of $3.5 \times 10^6$ cells was obtained, performing a treatment with Trizol compound (Invitrogen). 0.5 µg of RNA was used to generate the cDNA by reverse transcription reaction with the PrimeScript™ 1st Strand cDNA Synthesis kit, which uses isotype-specific universal primers. The antibody heavy and light chain were amplified according to the GenScript rapid amplification of cDNA ends (RACE) standard operating procedure (SOP). Amplified antibody fragments were separately cloned into a standard cloning vector. PCR colony was performed to identify clones which have the correct size inserts. At least five colonies with inserts of the correct size were sequenced for each fragment. Sequences of different clones were aligned and the consensus sequence of these clones was provided. From this, nucleotide sequences of heavy and light chains of antibodies secreted by 2F11B1 hybridoma were determined, corresponding to those identified as SEQ ID NO. 1 and SEQ ID NO.3 to the light chains and sequences identified as SEQ ID NO. 1 and SEQ ID NO.3 to heavy chains.

Example 3: Flu Antigen Detection Assay, Specificity Determination of Flu Anti-PB2 Monoclonal Antibodies for Purified Flu Antigens by Indirect ELISA Assay This assay aims to demonstrate the specificity for Flu PB2 protein antibodies produced by 1A3E2 and 2F11B1 hybridomas. Antigen detection was carried out using the indirect ELISA technique, where ELISA plate was activated with 50 ng of purified antigen for 1 hour at 37° C. (98.6° F.). Similarly, the plate was activated with 20 μg of uninfected MDCK cell lysate (as a negative control) and infected with Flu serotype A virus. Another negative control included was 50 ng of ADV pIII protein in a separate well. Subsequently, the plate was washed twice with 1×/Tween20 0.05% phosphate buffered saline (PBS). The plate was then blocked for 2 hours at 37° C. (98.6° F.) with 1×PBS/10% Fetal Bovine Serum (FBS). Subsequently, the washes were repeated and then each antibody (1A3E2 and 2F11B1) were incubated at a final concentration of 3.4 μg/mL (170 ng per well), diluted in 1×PBS/10% FBS, for 1 hour at 37° C. (98.6° F.) (each antibody on a separate plate). Under the same conditions, on a different plate, a control assay was performed using a commercial monoclonal antibody that recognizes the PB2 protein of Flu (Anti-Influenza A virus PB2 protein antibody, catalog number GTX125926, GeneTex) at a concentration of 3.4 μg/mL. After incubation time, the washes were repeated and a secondary anti-mouse IgG antibody labeled with horseradish peroxidase (HRP) in dilution 1 in 2000 (1.8 ng/μl per well) was added to each well in 1×PBS/10% FBS, for 1 hour at room temperature (≈25° C. (77° F.)), in the dark. Finally, washes were carried out and it was developed with 50 μL of citrate/tetramethyl-benzidine buffer (TMB, 3,3',5,5'-tetramethylbenzidine, 1 mg/mL, Becton Dickinson). To stop the reaction, 50 μL of $H_2SO_4$ 2 N were added and the result was read on an ELISA reader, at 450 nm. To determine that the reaction of the secondary antibody was specific in recognizing the primary antibody and also that the obtained signal was not caused by nonspecific binding of the secondary antibody to the viral antigen, controls were carried out in which only the secondary antibody was used with no primary antibody or sample (well not activated). Another control to determine that the primary antibody reaction is specific for the antigen, consisted of using the antibodies on an ELISA plate that has not been activated with the antigen (with no antigen) or using the antibodies on an ELISA plate that possessed 50 ng of ADV pIII protein or uninfected cells. Results show that monoclonal antibodies of the invention are capable of recognizing 50 ng of purified antigen, specifically, since they do not recognize ADV pIII protein, nor proteins of uninfected cells (FIGS. 1A and 1B). On the other hand, it was observed that commercial antibody (FIG. 1C) used in the assay as a control, although it was specific for the detection of infected cells only, it was not efficient in detecting purified Flu recombinant PB2 protein in our laboratory. All negative controls used gave expected results (data not shown in the figures).

Example 4: Assay to Determine Monoclonal Antibodies Sensitivity for the Detection of Flu Anti-PB2 Viral Antigens Assay was performed to determine the maximum protein dilution that Flu anti-PB2 monoclonal antibodies from 1A3E2 and 2F11B1 hybridomas are able to detect by indirect ELISA. For this, the same technique described in example 3 was used. The plate was activated with 11 serial dilutions of Flu PB2 protein 1:2, starting with 50 ng of purified antigen. Anti-PB2 1A3E2 and 2F11B1 antibodies were used in a concentration of 3.4 μg/mL (170 ng/well), and were diluted in 1×PBS/10% FBS. Subsequently, anti-mouse IgG detection antibody was added in a dilution of 1:2,000 (1.8 ng/μL per well) and incubated for 1 hour at room temperature (≈25° C. (77° F.)), in the dark. Finally, the washes were carried out and it was developed with 50 μL of citrate/Tetramethylbenzidine (TMB, 3-3'-5-5'-tetramethylbenzidine, 1 mg/mL, Becton Dickinson) buffer. To stop the reaction, 50 μL of $H_2SO_4$ 2 N were added and the result was read on an ELISA reader, at 450 nm. Results showed that anti-PB2 1A3E2 antibody is capable of detecting up to 780 picograms (pg) of the Flu PB2 protein (FIG. 2A). Anti-PB2 antibody from 2F11B1 hybridoma showed the same sensitivity as anti-PB2 1A3E2 antibody (FIG. 2B). Controls were included in all the tests which allowed to rule out non-specific reactions of both the antibodies, which contained all components of the test except the sample (Flu PB2 protein, data not shown in the graphs).

Example 5: Assay to Determine Monoclonal Antibodies Efficiency to Detect Flu Viral Antigens, by Indirect ELISA Assay was performed to determine the maximum dilution of Flu anti-PB2 monoclonal antibodies from 1A3E2 and 2F11B1 hybridomas which allow the detection of the viral antigen. For this, a plate was activated with 50 ng of purified antigen (protein PB2) and then the plate was blocked for 2 hours at 37° C. (98.6° F.) with 1×PBS/10% Fetal Bovine Serum (FBS). Anti-PB2 1A3E2 and 2F11B1 antibodies were used in 1:2 dilutions, starting from the working concentration (170 ng) up to dilution 11 (0.15 ng) in 1×PBS/10% FBS. Subsequently, anti-mouse IgG detection antibody was added in a dilution of 1:2000 (1.8 ng/µL per well) incubated for 1 hour at room temperature ($\approx$25° C. (77° F.)), in the dark. Finally, the washes were carried out and it was developed with 50 µL of citrate/Tetramethylbenzidine (TMB, 3-3'-5-5'-tetramethylbenzidine, 1 mg/mL, Becton Dickinson) buffer. To stop the reaction, 50 µL of $H_2SO_4$ 2 N were added and the result was read on an ELISA reader, at 450 nm. In FIG. 3 is observed that anti-PB2 1A3E2 antibody can detect 50 ng of the purified antigen up to 1.3 ng per well (FIG. 3A). On the other hand, the anti-PB2 2F11B1 clone is more efficient than the 1A3E2 clone, since it recognizes 50 ng of purified PB2 with almost all the dilutions made (FIG. 3B). Negative control included in this assay corresponds to a well which does not contain sample (protein PB2), was blocked with 1×PBS/10% FBS, primary antibody (anti-PB2 1A3E2 or anti-PB2 2F11B1) was added and also contains HRP-conjugated anti-mouse IgG antibody.

Example 6: Clinical Diagnosis of Samples from Flu-Infected Patients, Using Flu Anti-PB2 Monoclonal Antibodies, Using ELISA Sandwich Technique Availability and concentration of viral proteins is generally very low in clinical samples of nasopharyngeal swabs, so it was necessary to modify the ELISA assay that was previously performed. For this assay, a Sandwich ELISA was performed, using anti-PB2 antibody from the Flu 1A3E2 hybridoma as capture antibody and Flu anti-PB2 2F11B1 clone as detection antibody. Flu anti-PB2 2F11B1 detection antibody was conjugated to the HRP. Wells of an ELISA plate were activated with 3.4 µg/mL (170 ng/well) of anti-PB2 antibody from Flu 1A3E2 hybridoma, diluted in 1×PBS, for 1 hour at 37° C. (98.6° F.). 2 washes were carried out with 1×-Tween20 PBS 0.05% and later the plate was blocked with 200 µL of 1×PBS/10% FBS for 1 hour at 37° C. (98.6° F.). Washed again and incubated for 1 hour at 37° C. (98.6° F.) each well with 50 µL of nasopharyngeal swabs (previously treated) from patients positive for Flu according to the diagnostic method "$D^3$ Ultra DFA Respiratory Virus Screening and ID ( ) Kit de DHI (Diagnostics Hibryds) USA", routinely referred to as "viral panel", and which were treated as described later. As controls were included: 1) specificity control: 50 µL of sample of patients diagnosed with Flu were used by the viral panel for anti-Flu antibodies; 2) positive control: 50 ng of recombinant PB2-Flu protein; 3) Negative control: corresponding to healthy control samples. Subsequently, the 2 corresponding washes were carried out with 1×-Tween20 PBS 0.05% and each well was incubated for 1 hour at room temperature with 50 µl of anti-PB2 antibody from 2F11B1 hybridoma, conjugated with HRP (1.8 ng/µL of final concentration). Detection antibodies were incubated for 1 hour at room temperature ($\approx$25° C. ($\approx$77° F.)), in the dark. The plate was then washed 2 more times, developed with 50 µL of TMB solution and incubated for 15 minutes in the dark. The reaction stopped with 50 µL of H2SO4 2N and the plate was read at 450 nm in an ELISA reader (Epoch model), certified for clinical diagnosis.

Figure 4:
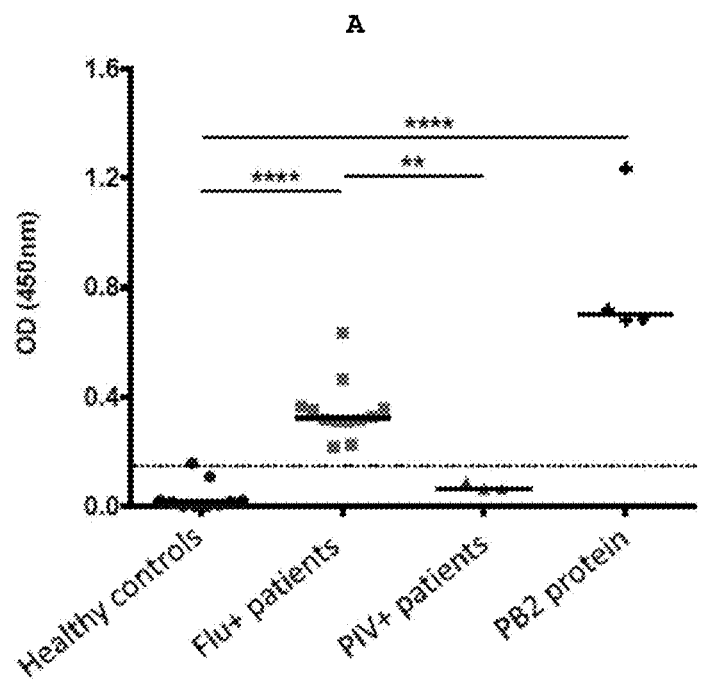
FIG. 4: Flu detection in clinical samples by ELISA Sandwich, using the combination of monoclonal antibodies secreted by 1A3E2 and 2F11B1 hybridomas. ELISA plates were activated with 170 ng of secreted antibody by 1A3E2 hybridoma (anti-Flu), functioning as capture antibody. Activated wells with capture antibody were incubated with 50 µL of nasopharyngeal swab (NPS) samples from patients with viral respiratory symptoms. As negative controls, 10 samples of healthy controls were analyzed. 12 samples of patients Flu-positive were used and as a specificity control, 3 samples of parainfluenza virus positive patients were included. As a positive control, wells were included to which purified Flu recombinant PB2 protein was added. For the detection of captured protein by 1A3E2 antibody, antibodies produced by 2F11B1 hybridoma, conjugated to the Horseradish Peroxidase enzyme, were used in a 1:2000 dilution (1.8 ng/µL per well). Data shown the median value of emitted absorbance at 450 nm of each sample (P<0.01 and **P<0.0001; using the non-parametric student test and Mann Whitney post test comparing Flu positive patients versus healthy controls, and against viruses used as specificity control).
Figure 5:
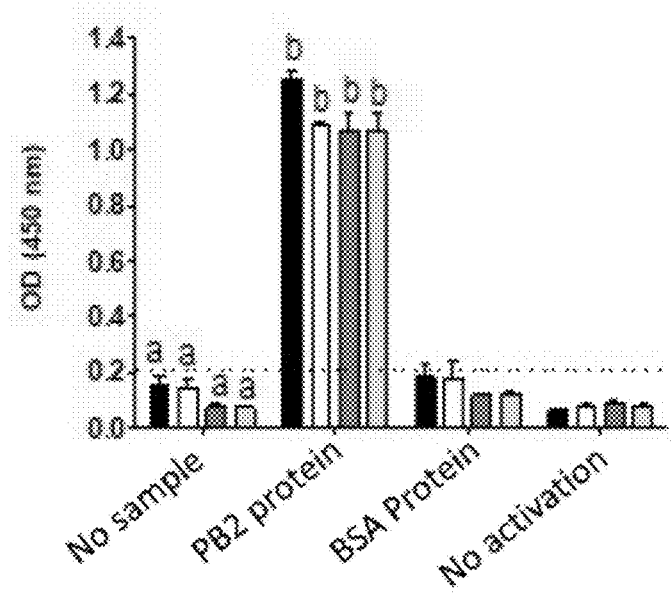
FIG. 5: Protein PB2 detection by indirect ELISA, using monoclonal antibodies secreted by biotin-conjugated 1A3E2 and 2F11B1 hybridomas. PB2 protein detection of Biotin-conjugated antibodies is observed. Antibody fragments secreted by 1A3E2 and 2F11B1 hybridomas are indicated in black and white respectively. While activity of the complete fragments of antibodies secreted by 1A3E2 and 2F11B1 hybridomas respectively is shown in gray. Data shown in graph express absorbance at 450 nm emitted by the conversion of substrate Tetramethylbenzidine to a colored compound catalyzed by the Horseradish peroxidase (HRP) enzyme. Average value of emitted absorbance at 450 nm of each sample is shown (where b is equal to p<0.0001 compared to a; by means of the 2-way ANOVA test comparing the well with no sample versus well with protein with all antibodies).

Obtained results for this test are shown in FIG. 4A, where it can be observed that the ELISA Sandwich technique using the antibody (anti PB2) from 1A3E2 hybridoma, as capture antibody and the antibody from the 2F11B1-HRP hybridoma as detection antibody, allows the detection of the antigen in samples of Flu-infected patients (FIG. 4A), which were previously confirmed by direct immunofluorescence in a certified clinical laboratory using the viral panel. FIG. 4A, shows the obtained results with Flu anti-PB2 antibodies, where 12 samples from patients diagnosed as positive PIV were used and as a specificity control, 3 samples from patients positive for the Influenza virus were included. As a positive control, wells were included to which purified Flu recombinant PB2 protein was added. As negative control, 10 healthy controls were analyzed. Results show that antibodies are specific in detecting only Flu-positive patients and not healthy controls or those infected with another virus (PIV). All samples detected positive by ELISA are those that show an optical density (OD) above 0.15.

This assay demonstrates the versatility of the antibodies from 1A3E2 and 2F11B1 hybridomas Flu anti-PB2, since they are capable of simultaneously binding to the antigen without competing for the binding site or interfering with each other. The above allows the capture and subsequent detection of PB2 protein in patient samples.

Treatment of clinical samples. The samples used for the tests were obtained from nasopharyngeal swabs contained in universal transport medium (UTM). The samples were centrifuged at 14,000 rpm for 4 minutes at room temperature. Subsequently, the supernatant (SN1) was separated from the pellet; the latter was incubated with 100 µL of RIPA Buffer (50 mM Tris-HCl pH 8.0, 150 mM NaCl, 1% NP-40, 0.5% Sodium Deoxycholate, 0.1%, SDS and a 1× protease inhibitor cocktail) for 15 minutes at 4° C. (39.2° F.), vortexing every 5 minutes. It was then centrifuged at 14,000 rpm for 4 minutes at room temperature. At the end, the supernatant obtained (SN2) was taken and mixed with SN1, vortexing was performed.

It is extremely important to use both antibodies for the detection of PB2 protein, due to the low availability of antigen in the sample. Using an ELISA Sandwich increases the specificity and sensitivity in the diagnosis of Flu. Assays were performed where the plate was activated directly with clinical samples of nasopharyngeal swabs, then anti-PB2 1A3E2 and anti-PB2 2F11B1 antibodies were incubated, separately. Then a secondary anti-mouse IgG antibody conjugated with HRP was incubated and absorbance generated by incubating the antibody complex plus sample with the TMB substrate was evaluated, and a positive diagnosis was not observed since the signal delivered was very low (data not shown).

Carrying out a diagnostic kit using the ELISA's Sandwich technique, where the plate can be activated and blocked, would reduce the time and cost of performing a diagnosis, since this technique is easy to perform and analyze compared to the standard technique (PCR). The kit does not need highly trained personnel to perform or analyze it.

Example 7: Clinical Diagnosis of Samples from FLU-Infected Patients, Using FLU Anti PB2 Monoclonal Antibodies, by Luminex Sandwich-Type As in ELISA technique, the availability and concentration of viral proteins is generally very low in clinical samples of nasopharyngeal swabs, so it was wanted to evaluate the obtained results by ELISA technique to another more sensitive technique (FIG. 4A). For this assay, a Sandwich-type luminex assay was performed, using anti-PB2 1A3E2 antibody as capture antibody and anti-PB2 2F11B1 as detection antibody. FLU anti-PB2 2F11B1 detection antibody was conjugated to the fluorophore biotin. Luminex plates were activated with 50 magnetic microspheres per (internally labeled with red or near infrared fluorophore of different intensities) per µL, which were conjugated with the antibody secreted by 1A3E2 hybridoma (anti-FLU), functioning as a capture antibody (at a final concentration of 2.5 µM). Conjugated microspheres were incubated with 50 µL of nasopharyngeal swab (NPS) samples from patients with viral respiratory symptoms, for 2 hours at room temperature (□23° C. (□73.4° F.)), stirring at 400 rpm and in the dark (covered with aluminum foil). As negative controls, 8 samples of healthy controls were analyzed. 19 samples of patients positive for Flu were used (according to the diagnostic method "$D^3$ Ultra DFA Respiratory Virus Screening and ID Kit de DHI (Diagnostics Hibryds) USA", routinely referred to as "viral panel", which were treated as the same way mentioned above, and as a positive control, wells were included to which purified PB2-FLU protein (50 ng) was added. After 2 hours, 2 washes are carried out again with 100 µL 1×-Tween20 PBS 0.05% for 30 seconds using the manual magnetic scrubber. For detection of protein captured by 1A3E2 antibody, antibodies produced by 2F11B1 hybridoma, conjugated to biotin fluorophore, were used at a concentration of 4 µg/mL diluted in 1×PBS-1% BSA, the wells being incubated with 50 µL. Incubation is carried out for 1 hour at room temperature, in the dark, stirring at 400 rpm. 2 washes are carried out again with 100 µL 1×-Tween20 PBS 0.05% for 30 seconds using the manual magnetic scrubber. The complex formed by conjugated microspheres with capture antibody plus antigen and detection antibody is incubated with 50 µL of Streptavidin/Phycoerythrin at a final concentration of 6 µg/mL. Incubation is carried out for 30 minutes at room temperature, in the dark, stirring at 400 rpm. Finally, two more washing steps are carried out and the wells are incubated with 100 µL of Sheat fluid reagent (reagent used by Luminex equipment for the equipment to read the samples), stir 5 minutes at 400 rpm, in the dark. Results of the mean fluorescence intensity (MFI) are then read on the Luminex 200 equipment, which, through a red laser (621 nm), detects the recognition region of the microsphere and the Green laser (511 nm) detects the binding of the detection antibody to the analyte.

Obtained results for this test are shown in FIG. 4B, where it can be observed that the Luminex technique, as the obtained by ELISA technique using the antibody (anti PB2) from 1A3E2 hybridoma, as capture antibody and the antibody from the 2F11B1-HRP hybridoma as detection antibody, allows the detection of the antigen in samples of FLU-infected patients (FIG. 4B) with high intensity, which were previously confirmed by direct immunofluorescence in a certified clinical laboratory using the viral panel. FIG. 4B, shows the obtained results with FLU anti-PB2 antibodies, where 19 samples from patients diagnosed as positive FLU were used and 6 healthy control samples. Furthermore, as a positive control, wells were used to which purified PB2-FLU protein was added. Results show that anti-PB2 antibodies are specific in detecting only Flu-positive patients and not control subjects. All samples detected as positive by Luminex are those that show an MFI above two standard deviations from the mean MFI of healthy controls.

This assay, as in ELISA assay with patient samples, demonstrates the versatility of antibodies from 1A3E2 and 2F11B1 hybridomas of FLU, since they are capable of simultaneously binding to antigen without competing for the binding site or interfere with each other and detect poor antigen availability in nasopharyngeal swab sample.

Example 8: Blind Study for the Detection of PB2-FLU Antigen in Clinical Samples, Obtained from Patients with an Infection, Using Flu Anti-PB2 Monoclonal Antibodies, which are Part of the Respiratory Virus Multiple Detection Kit Previously, ELISA tests were carried out in Sandwich where the previous diagnosis of the samples to be evaluated was known. After these tests, a blind study was carried out, where about 160 nasopharyngeal swab samples were evaluated, without knowing the microbiological diagnosis. For all assays in the blinded study, ELISA's Sandwich were performed where anti-L 1A3E2 antibody was used as capture antibody and anti-L 2F11B1 antibody was used as HRP-conjugated detection antibody. For all assays, wells of an ELISA plate were activated with 3.4 µg/mL (170 ng/well) of anti-L antibody from FLU 1A3E2 hybridoma, diluted in 1×PBS, for 30 minutes at 37° C. (98.6° F.). 2 washes were carried out with 1×-Tween20 PBS 0.05% and later the plate was blocked with 200 µL of 1×PBS/10% FBS for 30 minutes at 37° C. (98.6° F.). Each well with 50 µL of nasopharyngeal swabs from patients was washed again and incubated for 1 hour at 37° C. (98.6° F.), which were evaluated in parallel by the standard diagnostic method (PCR), routinely referred to as "viral panel", and which were treated as previously described in example 6. As controls were included: 1) specificity control: 50 µL of BSA protein (50 ng) were used; 2) positive control: 50 ng of PB2-FLU recombinant protein; 3) Negative controls: wells with no sample and wells blocked and incubated with detection antibody. Subsequently, the 2 corresponding washes were carried out with 1×-Tween20 PBS 0.05% and each well was incubated for 30 minutes at room temperature (≈25° C. (≈77° F.), in the dark) with 50 µl of anti-PB2 antibody from 2F11B1 hybridoma, conjugated with HRP (1.8 ng/µL of final concentration). The plate was then washed 2 more times, developed with 50 µL of TMB solution and incubated for 15 minutes in the dark. The reaction stopped with 50 µL of $H2SO_4$ 2 N and the plate was read at 450 nm in an ELISA reader (Epoch model), certified for clinical diagnosis.

Results are shown in FIG. 4A, where the ability of antibodies to detect protein PB2 in clinical samples is observed, since they were designed from a chimera protein. 18 out of 21 PIV positive patients were detected, and from these results the diagnostic accuracy of antibodies could be determined, which is shown in Table 1. The table shows the two concepts that define diagnostic accuracy, where we have specificity, that is, the ability of antibodies to diagnose negative samples as negative, without detecting false positives, and on the other hand, we have sensitivity, that is, the ability of antibodies to diagnose as positive those samples that really are, without diagnosing false negatives. Exposed results in the table show a high specificity (94%) and sensitivity (86%) percentage of antibodies against the standard technique (PCR).

TABLE 1

Diagnostic accuracy of anti-PB2-FLU antibodies

| PIV (N = 160) | Diagnosis by reference technique: PCB | | Specificity | Sensitivity |
|---|---|---|---|---|
| Diagnostic test: ELISA | True positives 18 | False positives 9 | 100% | 86% |
| | False negatives 3 | True negatives 130 | | |

Example 9: Protein PB2 Detection by Indirect ELISA Assay, Using Complete Monoclonal Antibodies or Fragments Thereof In this application example, is demonstrated that both the specific monoclonal antibody against the PB2 protein can be detected by indirect ELISA. For detection of protein L, ELISA plates were activated with 50 µL of protein PB2 y BSA 50 ng. Nonspecific sites were blocked with 10% FBS diluted in 1×PBS. 170 ng (3.4 µg/mL) of Fab fragments of antibodies secreted by 1A3E2 (anti-Flu) and 2F11B1 (anti-Flu) hybridomas, both previously biotin conjugated. Incubation of biotin-binding molecules (Streptavidin), which is HRP-conjugated (1:2,000 dilution, 75 ng per well) (FIG. 5, dark gray bar, 1A3E2 antibody and light gray bar, 2F11B1 antibody).

Example 10: Flu Antigen Detection Assay, Using F(Ab')2 Fragments of Flu Anti-PB2 Monoclonal Antibodies by Indirect ELISA The objective of this assay is to demonstrate the ability to detect fragments of anti-Flu antibodies, produced by 1A3E2 and 2F11B1 hybridomas, by PB2 protein. Prior to the indirect ELISA assay, IgG molecule of each anti-Flu antibody was fragmented. Fragmentation was performed using the "Thermo Scientific™ Pierce™ $F(ab')_2$ Fragment Preparation Kits" kit (#10381214, Thermo Scientific), which separates $F(ab')_2$ fragment and Fc from the antibody of interest, by using the enzyme pepsin that digests the Fc fragment and subsequently purification steps are carried out to separate the $F(ab')_2$ fragment from the digested Fc fragment. After antibody fragmentation, purified $F(ab')_2$ fraction was verified by the Western bolt technique. $F(ab')_2$ fractions were conjugated to biotin molecules using the rapid conjugation kit, Lightning-Link rapid biotin type A (#370-0010, Expedeon). Having ready all reagents, antigen detection was carried out by indirect ELISA technique, where ELISA plate was activated with 50 ng of purified PB2 antigen for 1 hour at 37° C. (98.6° F.). Two negative controls were included, one with no sample and the other incubating the well with 50 ng of BSA protein. Subsequently, the plate was washed twice with 1×/Tween20 0.05% phosphate buffered saline (PBS). The plate was then blocked for 2 hours at 37° C. (98.6° F.) with 1×PBS/10% Fetal Bovine Serum (FBS). Subsequently, the washes were repeated and then each antibody conjugated with biotin, unfractionated and $F(ab')_2$ fractions (1A3E2 and 2F11B1) was incubated at a final concentration of 3.4 µg/mL (170 ng per well), diluted in 1×PBS/10% FBS, for 1 hour at 37° C. (98.6° F.) (each antibody on a separate plate). After incubation time, washings were repeated and a biotin-binding protein (Streptavidin) labeled with horseradish peroxidase (HRP) enzyme was added to each well in dilution 1 in 2000 (25 ng/µL per well) in 1×PBS/10% FBS, for 1 hour at room temperature (□25° C. (□77° F.), in the dark. Finally, the washes were carried out and it was developed with 50 µL of citrate/Tetramethylbenzidine (TMB, 3-3'-5-5'-tetramethylbenzidine, 1 mg/mL, Becton Dickinson) buffer. To stop the reaction, 50 µL of $H_2SO_4$ 2 N were added and the result was read on an ELISA reader, at 450 nm. To determine that the reaction of the secondary antibody was specific in recognizing the primary antibody and also that the obtained signal was not caused by nonspecific binding of the secondary antibody to the antigen, controls were carried out in which only the secondary antibody was used with no primary antibody or sample (well not activated). Another control to determine that the primary antibody reaction is specific for the antigen, consisted of using the antibodies on an ELISA plate that has not been activated with the antigen (with no sample) or using the antibodies on an ELISA plate that possessed 50 ng of PB2. Results show that monoclonal antibodies of the invention are capable of recognizing 50 ng of purified antigen, specifically, regardless of whether the complete antibody or a fragment thereof is used (FIG. 5, black bar, 1A3E2 antibody and white bar, 2F11B1 antibody).

The invention claimed is:

1. A monoclonal antibody or an antigen-binding portion thereof that binds to human influenza A virus (Flu) protein PB2 for use in detecting the presence and/or localization of the protein, wherein the antibody is selected from:

i) an antibody comprising a light chain variable region where its CDR1 ($CDR_{LC1}$) is defined according to SEQ ID NO: 1, its CDR2 ($CDR_{LC2}$) is defined by SEQ ID NO: 2 and its CDR3 ($CDR_{LC3}$) corresponds to SEQ ID NO: 3, and a heavy chain variable region where its CDR1 (CDR$_{HC1}$) is defined according to SEQ ID NO: 4, its CDR2 (CDR$_{HC2}$) is defined by SEQ ID NO: 5 and its CDR3 (CDR$_{HC3}$) corresponds to SEQ ID NO: 6, or ii) an antibody comprising a light chain variable region where its CDR1 (CDR$_{LC1}$) is defined according to SEQ ID NO: 7, its CDR2 (CDR$_{LC2}$) is defined by SEQ ID NO: 8 and its CDR3 (CDR$_{LC3}$) corresponds to SEQ ID NO: 9, and a heavy chain variable region where its CDR1 (CDR$_{HC1}$) is defined according to SEQ ID NO: 10, its CDR2 (CDR$_{HC2}$) corresponds to SEQ ID NO: 11 and its CDR3 (CDR$_{HC3}$) corresponds to SEQ ID NO: 12, wherein said antibody can be used as detection or capture antibody.

2. A method to detect Flu virus in a biological sample comprising contacting the biological sample with the monoclonal antibody or an antigen-binding portion thereof that binds to human influenza A virus PB2 protein of claim 1 and detecting the binding of the antibody to antigen, thereby detecting the Flu virus in the sample.

3. The method to detect Flu virus in a biological sample according to claim 2, wherein the biological sample is selected from the group consisting of in vitro cells infected with Flu, nasal secretions, nasal washes, cerebrospinal fluid, pharyngeal secretions and/or bronchial washes or secretions.

4. The method to detect Flu virus in a biological sample according to claim 2, wherein an assay used to detect the binding of the antibody to antigen is selected from: ELISA, immunofluorescence, immunohistochemistry, immunochromatography, flow cytometry, cell sorter, immunoprecipitation and/or Western blot.

5. The method to detect Flu virus in a biological sample according to claim 2, wherein the antibody or an antigen-binding portion thereof is conjugated with a marker that allows its detection.

6. The method to detect Flu virus in a biological sample according to claim 5, wherein the antibody is conjugated to a marker selected from the group consisting of fluorophores, biotin, radioisotopes, metals and enzymes.

7. A kit for qualitative and/or quantitative detection of Flu virus comprising:
a monoclonal antibody or an antigen-binding portion thereof that binds to human influenza A virus PB2 according to claim 1, which acts as a capture or detection antibody, wherein the detection antibody is conjugated to a marker for its detection;
a solid support to which the capture antibody is attached; and
reagents for detecting the marker conjugated to the detection antibody, wherein the marker is selected from the group consisting of fluorophores, biotin, radioisotopes, metals, and enzymes.

8. The kit for qualitative and/or quantitative detection of Flu virus according to of claim 7, wherein the solid support is a membrane formed by one of the compounds selected from the group consisting of nitrocellulose, cellulose, polyethylene and nylon.

9. The kit for qualitative and/or quantitative detection of Flu virus according to claim 7 wherein the detection of human influenza A virus PB2 is carried out with an immunochromatographic test, luminex, flow cytometry, immunofluorescence, radioimmunoanalysis, Western blot, Dot blot, ELISA, immunodiffusion or immunoprecipitation.

* * * * *